United States Patent [19]

Shearing

[11] Patent Number: 4,834,754
[45] Date of Patent: May 30, 1989

[54] INTRAOCULAR LENS

[76] Inventor: Steven P. Shearing, 2575 Lindell, Las Vegas, Nev. 89102

[21] Appl. No.: 168,131

[22] Filed: Mar. 14, 1988

Related U.S. Application Data

[60] Continuation-in-part of Ser. No. 6,804, Jan. 27, 1987, abandoned, which is a division of Ser. No. 693,108, Jan. 22, 1985, Pat. No. 4,657,546, which is a continuation-in-part of Ser. No. 511,906, Jul. 8, 1983, abandoned.

[51] Int. Cl.4 .............................................. A61F 2/16
[52] U.S. Cl. ...................................................... 623/6
[58] Field of Search ............................................ 623/6

[56] References Cited

U.S. PATENT DOCUMENTS

| | | | |
|---|---|---|---|
| 2,834,023 | 5/1958 | Lieb | 623/6 |
| 4,139,915 | 2/1979 | Richards et al. | 623/6 |
| 4,439,873 | 4/1984 | Poler | 623/6 |
| 4,450,593 | 5/1984 | Poler | 623/6 |
| 4,605,409 | 8/1986 | Kelman | 623/6 |
| 4,608,049 | 8/1986 | Kelman | 623/6 |

Primary Examiner—Ronald L. Frinks
Attorney, Agent, or Firm—Jerry R. Seiler

[57] ABSTRACT

An intraocular lens comprises an optical lens body having a plurality of lens segments held together by a thin flexible material secured to one of the lens body surfaces and to at least two of the lens segments. The lens body may be temporarily folded by overlapping the lens segments and inserting a folded lens through a corneal incision.

15 Claims, 2 Drawing Sheets

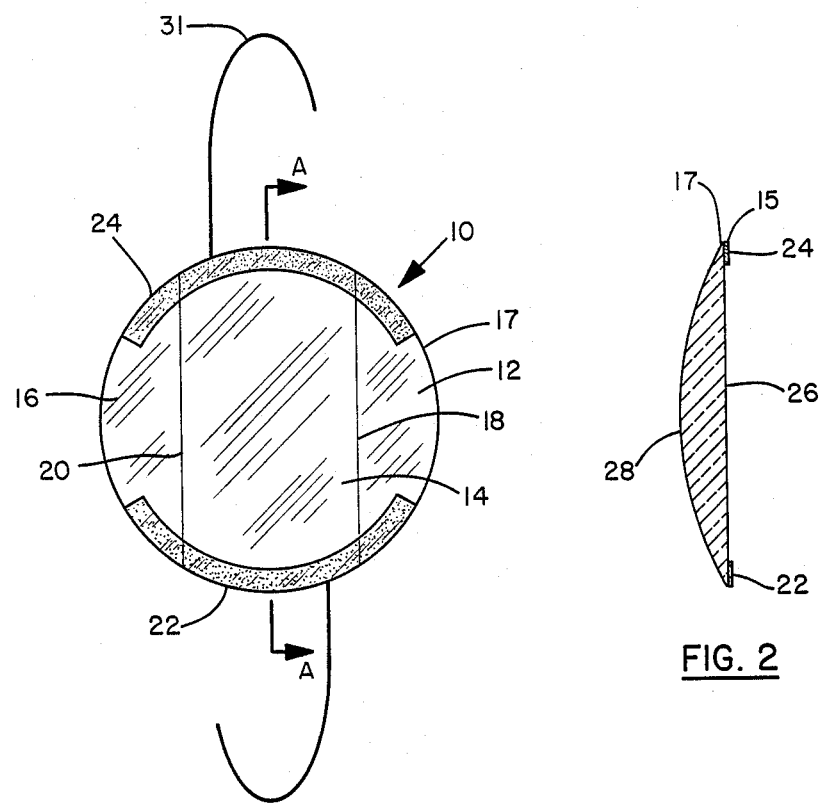
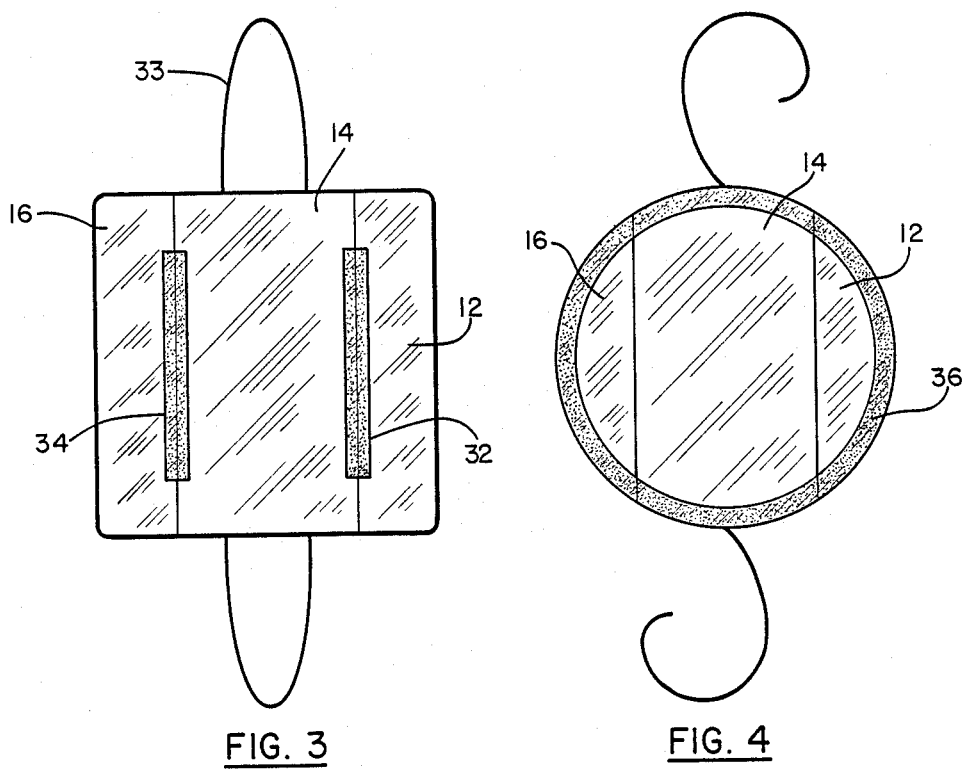

INTRAOCULAR LENS

REFERENCE TO PRIOR APPLICATIONS

This application is a continuation-in-part of my copending application Ser. No. 006,804, filed Jan. 27, 1987, now abandoned which is a divisional of application Ser. No. 693,108, filed Jan. 22, 1985, U.S. Pat. No. 4,657,546 which was a continuation-in-part of Ser. No. 511,906, filed July 8, 1983, abandoned.

BACKGROUND OF THE INVENTION

In my aforesaid prior patent and application Ser. No. 006,875, now U.S. Pat. No. 4,725,278, there is disclosed an intraocular lens comprising a segmented lens body wherein the lens may be folded for convenient insertion through a relatively small corneal incision for being transplanted in the posterior chamber of the eye. The segments of the lens body are secured together using a membrane or thin sheet of optical quality material such as silicone. The lenses of the present invention comprise further improvements of such a segmented lens.

BRIEF DESCRIPTION OF THE DRAWINGS

FIG. 1 is a front view of a lens body made up of a plurality of segments and secured using two pieces of thin flexible material, each piece of material being secured to all of the segments;

FIG. 2 is a sectional view taken along lines A—A of FIG. 1;

FIGS. 3, 4, 5 and 7 illustrate additional embodiments of the invention; and

DETAILED DESCRIPTION OF THE INVENTION

Figure 5:
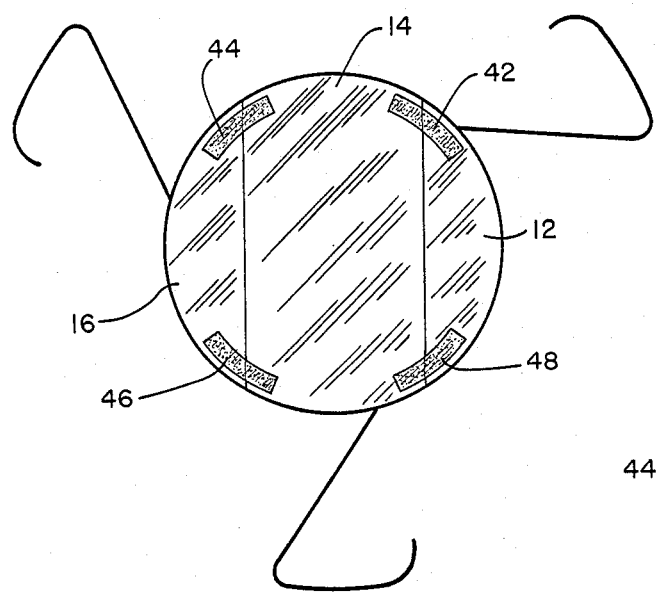

In FIGS. 1 and 2 there is illustrated a first embodiment of the invention comprising a optical lens 10 having three segments 12, 14, and 16. The lens segments are joined at interfacing edges 18 and 20, the lens being otherwise substantially as those disclosed in my aforesaid U.S. Pat. No. 4,567,546, the descripton of which is incorporated herein by reference. In order to achieve a folded lens assembly within suitable dimensions, the greatest thickness of the center lens segment, the thickest segment in a convex lens, should be about 1 mm or less. The preferred lens is also formed of three lens segments, a center segment and two side segments, so that the center segment is free of distortion and without segment interfaces at or very near the center of the lens. To produce lens of maximum 1 mm or less thickness will require use of optical quality material of relatively high index of refraction of 1.5 or greater and more preferably 1.6 or more. Suitable materials having such a high refractive index include optical quality polysulfone, polycarbonate and high quality optical glass as well as other suitable materials known in the art. The width of the lens segments should also be such that the two side segments can be folded without being substantially overlapped which would unduly increase the cross-sectional thickness of the folded lens, thereby at least partially defeating the purpose of the invention. Thus, for example, where the overall lens body diameter is between about 4 and 7 mm, preferably about 6.0 mm, a center lens segment having a width between about 2.0 and 3.5 mm with side segments each being between about 1.25 and about 2.0 mm is quite suitable to avoid such overlap. However, some overlap is permissible where it does not increase the thickness beyond the aforesaid limits.

In the improved lens of the present invention a discrete thin body of flexible material or membrane for joining the lens segments together covers only a portion of the lens body surface to which it is secured. In other words, the material component for holding the lens segments together cover less than the entire surface on one side of the lens body.

Figure 6:
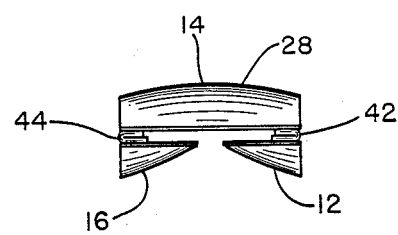
FIG. 6 is a top view of the lens of FIG. 5 showing the two side segments folded to overlap the center segment for being inserted in a corneal incision for transplant.

The material for holding the lens components together, and which facilitates the segments being folded for insertion into the eye and then unfolded to result in a useful implanted lens in which all of the segments lie along a single common plane, comprises one or more strips or pieces of thin, flexible material. The material used for securing the lens segments together may be of optical quality, transparent or it may be of non-optical or nontransparent material. However, it must be thin and flexible so that it does not create any substantial bulk or thickness relative to the thickness to the lens body itself. It must also be flexible so that it can act as a hinge when the lens is folded as illustrated in FIG. 6. Moreover, the material must be biocompatible, that is, it must be biologically inert, non-biodegradable and non-irritating when implanted in the eye. Suitable materials include synthetic resins such as polycarbonate, polysulfone, silicone, cellulose acetate, nylon, polyethylene, polypropylene, fluorocarbons such as tetrafluoroethylene fluorocarbon polymers or polyester film material commercially available as Mylar ®. For example, silicone material may be an optical silicone rubber such as hydroxy dimethylsilane, commercially available as Silarx ® and similar materials used for preparing contact lenses. Regardless of what material is used, it must be thin, i.e., a fraction of the thickness of the lens body components so that when the lens is folded, it does not take up significant space in the fold, and does not add substantial weight or bulk to the lens body.

The material may be secured to two or more segments, material pieces 22 and 24 shown in FIG. 1 each securing all three of the segments, at the bottom and top, respectively, of the lens body. In FIG. 3, two material pieces 32 and 34 each secure two of the lens body segments while in FIG. 4, a single material piece 36 secures all three lens segments.

In FIG. 5 there is illustrated yet another embodiment in which four material pieces 42, 44, 46, and 48 each secure two lens body segments together. The thin material pieces in the embodiments of FIGS. 1, 4 and 5 are preferred in that they do not extend substantially beyond the outer periphery of the lens body and also follow the contour of the outer lens body periphery. For example, in FIG. 1, the peripheral edge 17 of the lens body is substantially round and the material strips 22 and 24 are also arc-shaped so that the outer edges of each of the strips is shaped to follow the round circumferential shape of the lens body. In FIG. 4, the same round shape of the outer edge of material piece 36 follows the contour of the outer peripheral edge of the lens body. In FIG. 5, the material pieces do not extend entirely out to the edge of the lens body segments but are also shaped to follow the coutour of the lens body edge such that the outer edge of the pieces are substantially parallel with the peripheral lens body edge. The advantage of such a shape of the material pieces, secured as a plurality of pieces as illustated in FIGS. 1 and 5 or a single piece as shown in FIG. 4, is that material covers a relatively small amount or minimal surface area of the lens body. This is especially important where the material pieces are opaque, non-transparent or otherwise not of optical quality. Moreover, where the material pieces are secured to the lens body and the lens body segments adjacent or along the outer edge, they do not interfere substantially with the lens body optic. Accordingly, where the material pieces for securing the lens body segments and providing hinges for the segments to achieve a foldable lens body according to the invention are located adjacent or around a peripheral edge of the lens body, the requirement of the material of being of optical quality is not so important thereby substantially reducing the cost of the lens. To compensate for the presence of such less expensive material pieces, the lens body itself may be somewhat larger in area, for example, even 8 or 9 mm in diameter, without detracting from the advantage of the invention so long as the thickness of the lens body segment is not substantially increased and within the preferred dimensions previously described. With such relatively thin lens body segments, when the segments are overlapped as illustrated in FIG. 6 for implantation they still may be inserted into a relatively small corneal incision even though the diameter of the lens body is increased.

Figure 7:
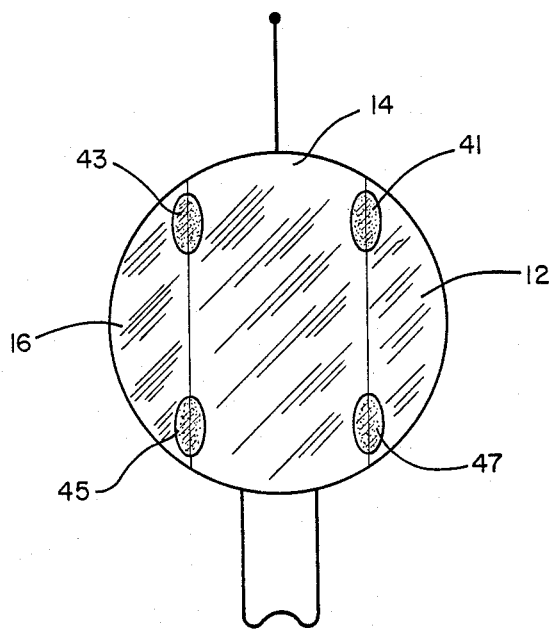

In FIGS. 3 and 7, there are shown other embodiments of strip materials acting as hinges and for securing adjacent lens body segments. Where such material strips are not shaped to follow the contour of the lens body edge, the desirability for using an optical quality material is preferred thereby avoiding possible interference with the lens optic. However, even where the material pieces are relatively small, for example, as shown in FIG. 7, if the lens body has a great enough surface area, non-optical quality material may still be suitably used as may be understood and selected by those skilled in the art.

In FIGS. 1, 3 and 5 there are also illustrated examples of different shaped haptics or support strands used to support the implanted lens in the eye. For example, the open strand 31 is shown in FIGS. 1 and 5, and any number of such strands may be used as well as different shapes thereof. Still other shaped support members such as further illustrated in FIGS. 3, 4 and 7 whether opened or closed may also be used. Thus, the number and shape of the haptic support members is not critical to the invention. Moreover, the shape of the lens body itself is not so important although a round or oval shaped lens body is preferred. A rectangular or square lens body as shown in FIG. 3 may also be used.

In FIG. 6 there is shown the lens body of FIG. 5 in a folded condition with segments 12 and 16 overlapping center segment 14, the segments being folded on hinges 42 and 44 with the lens body being viewed from the top. Because of the foldability of the lens of the invention, the shape of the lens body is preferably one in which the posterior surface is flat as shown in FIGS. 2 and 6 whereby the flat posterior surface facilitates the smallest folded size lens body. However, other lens body crosssectional shapes are not precluded according to the invention. The material pieces may be secured to either the posterior lens body surface or the anterior surface, but not both, since it would not provide an easily folded hinge. The material piece or pieces may be secured to the lens body by suitable means, especially laser or ultrasonic bonding, although chemical or solvent bonding may also be used. Such bonding techniques for the different materials described above will be known to those skilled in the art.

I claim:

1. An intraocular lens comprising an optical lens body having an anterior and a posterior surface comprising a plurality of lens segments, and a discrete thin body of flexible material secured to a single surface of said lens body and secured to at least two of said lens segments and wherein said material covers only a portion of said single surface and does not extend substantially beyond the peripheral edge of said lens body whereby the lens segments can be folded along interfacing edges of said lens segments.

2. The lens of claim 1 wherein said material comprises a single member secured entirely around the lens body adjacent said peripheral edge.

3. The lens of claim 1 wherein said material comprises a plurality of pieces, each piece being secured to at least two of said lens segments.

4. The lens of claim 3 wherein said pieces are secured to said lens body adjacent said peripheral edge.

5. The lens of claim 1 wherein said material comprises a thin sheet of biologically inert material.

6. The lens of claim 5 wherein said material is a synthetic resin selected from the group consisting of polycarbonate, polysulfone, silicone, cellulose acetate, nylon, polyethylene, polypropylene, fluorocarbon and polyester.

7. The lens of claim 6 wherein said material is of optical quality.

8. The lens of claim 5 wherein said material is chemically bonded to the lens body surface.

9. The lens of claim 5 wherein said material is laser bonded to the lens body surface.

10. The lens of claim 5 wherein said material is ultrasonically bonded to the lens body surface.

11. The lens of claim 2 wherein said material member has a peripheral edge of substantially the same shape as the shape of the the peripheral edge of said lens body.

12. The lens of claim 1 wherein said material is secured to the posterior surface of said lens body.

13. A process of preparing a lens of claim 1 comprising securing said material to the surface of said lens body by ultrasonic bonding.

14. A process of preparing a lens of claim 1 comprising securing said material to the surface of said lens body by laser bonding.

15. A process of implanting a lens of claim 1 comprising folding said lens body along interfacing edges of the lens segments until adjacent lens segments are overlapped, inserting the folded lens through a corneal incision, and unfolding said lens body whereby said lens segment lie in a common plane.

* * * * *